(12) United States Patent
Sogge et al.

(10) Patent No.: US 6,794,418 B2
(45) Date of Patent: Sep. 21, 2004

(54) METHOD AND PLANT FOR PRODUCTION OF OXYGENATED HYDROCARBONS

(75) Inventors: Jostein Sogge, Stjørdal (NO); Linda Bahr, Trondheim (NO); Bjørn Jarle Veland, Jar (NO); Ola Olsvik, Hundhamaren (NO)

(73) Assignee: Statoil ASA, Stavanger (NO)

( * ) Notice: Subject to any disclaimer, the term of this patent is extended or adjusted under 35 U.S.C. 154(b) by 164 days.

(21) Appl. No.: 10/169,420

(22) PCT Filed: Dec. 28, 2000

(86) PCT No.: PCT/NO00/00450

§ 371 (c)(1),
(2), (4) Date: Oct. 8, 2002

(87) PCT Pub. No.: WO01/47846

PCT Pub. Date: Jul. 5, 2001

(65) Prior Publication Data

US 2003/0092780 A1 May 15, 2003

(30) Foreign Application Priority Data

Dec. 28, 1999 (NO) .......................... 19996524

(51) Int. Cl.$^7$ .............................. C07C 27/00

(52) U.S. Cl. .................. 518/706; 518/702; 518/703; 518/704; 518/705

(58) Field of Search ...................... 518/700, 702, 518/703, 704, 705, 706

(56) References Cited

U.S. PATENT DOCUMENTS

| 4,546,111 A | 10/1985 | Banquy |
| 4,782,096 A | 11/1988 | Banquy |

FOREIGN PATENT DOCUMENTS

| CA | 2213025 | 4/1998 |
| EP | 123534 | 10/1984 |
| EP | 195200 | 9/1986 |
| EP | 0233076 | 8/1987 |
| EP | 0 650 950 A1 | 5/1995 |
| EP | 0 839 786 B1 | 5/1998 |
| JP | 57095926 | 6/1982 |

*Primary Examiner*—J. Parsa
(74) *Attorney, Agent, or Firm*—Kirkpatrick & Lockhart LLP

(57) ABSTRACT

A method for increasing production in an existing processing plant for converting natural gas into a product, wherein the natural gas is first converted into a synthesis gas in a synthesis gas section, the synthesis gas is reacted in a reactor for synthesis of the product, where non-converted synthesis gas and product are separated into two streams, where a product-rich stream is taken out of the process, while a product-poor stream is recycled as feed to the reactor together with make-up synthesis gas, and where a portion of the recycle stream is taken out of the recycle loop as a purge gas, where the purge gas is separated into hydrogen-rich and hydrogen-poor streams, where hydrogen-rich streams are introduced into steps in the process where it is desirable to have a supplement of hydrogen, and where the residual thermal value of the hydrogen-poor stream is optionally used for heating before it is discharged. A modified processing plant for carrying out the method is also described.

15 Claims, 2 Drawing Sheets

METHOD AND PLANT FOR PRODUCTION OF OXYGENATED HYDROCARBONS

CROSS REFERENCE TO RELATED APPLICATIONS

This application is based on international application No. PCT/NO00/00450, filed Dec. 28, 2000, having an International Publication Number of WO 01/47846 A1 and an International Publication Date of Jul. 5, 2001, which is based on Norwegian Patent Application No. 19996524, filed 28 Dec. 1999.

FIELD OF THE INVENTION

The present invention relates to a method for increasing production in an existing processing plant and to a processing plant that has been modified in order to carry out the method.

DESCRIPTION OF THE INVENTION BACKGROUND

Today, in the building of new processing plants, such as, e.g., plants for the production of methanol from natural gas or other suitable carbon sources, there is a clear trend towards building plants with an ever-increasing production capacity, such as more than 5000 tonnes of methanol each day. Thus, production costs are reduced due to economies of scale.

In areas where the price of natural gas is low, it is possible to produce methanol at a cost of as little as about USD 80 per tonne, and this is allowing methanol to obtain a foothold in a fuel market, i.e., for fuel cell cars and electricity production.

For existing processing plants that are too small in relation to current demands, there is a need to find solutions which allow an increase of total production and thus a reduction in production costs per unit without having to make major costly conversions and refits of the existing processing plant.

SUMMARY OF THE INVENTION

It is thus an object of the present invention to provide a method of increasing production in an existing processing plant without necessitating major, costly conversions of the existing plant, and to provide a processing plant that has been modified in order to carry out the present method.

According to the present invention, this is achieved by means of a method for increasing production in an existing processing plant for the conversion of natural gas to a product, wherein the natural gas is first converted to a synthesis gas in a synthesis gas section, the synthesis gas is reacted in a reactor for synthesis of the product, where non-converted synthesis gas and product are separated into two streams, where a product-rich stream is taken out of the process, whilst a product-poor stream is recycled as feed to the reactor together with make-up synthesis gas, and where a portion of the recycle stream is taken out of the recycle loop as a purge gas, where the purge gas is separated into hydrogen-rich and hydrogen-poor streams, where hydrogen-rich streams are introduced into steps in the process in which it is desirable to have a supplement of hydrogen, and where the residual thermal value of the hydrogen-poor stream may, if desired, be used for heating before it is discharged.

It is preferable that the synthesis gas from the synthesis gas section should be fed with a hydrogen-rich stream from the separated purge gas, and that this hydrogen-enriched synthesis gas should be passed through a new once-through reactor for production of the product and through a unit in order to separate a product-rich stream that is taken out, and a product-poor stream that is used as feed in the original reactor.

It is also preferable that the product-poor stream which is used as feed for the original reactor should be fed with additional synthesis gas that is produced in a separate secondary synthesis gas line.

The existin, reactor will preferably be operated virtually unchanged.

It is preferable that the secondary synthesis gas line should be based on ATR or POX.

It is also preferable that the product should be methanol or dimethyl ether.

Also provided is a processing plant for the production of a product based on natural gas, where the processing plant comprises a synthesis gas section for producing synthesis gas that mainly consists of CO, $CO_2$, $H_2$ and water, a synthesis section where the product is formed, and a purification section where the product is separated from unconverted reactants and other substances and purified, where unconverted reactants that are separated from the product are recycled to the synthesis section, and where a portion of the gas that is recycled is drawn off in a line in order to prevent build-up of inert gases, where the plant also comprises a separation unit for separating the gas that is drawn off in a line into hydrogen-rich and hydrogen-poor fractions, a line for conveying hydrogen-poor fractions to optional combustion and lines for leading hydrogen-rich fractions into the natural gas feed and for recycling to the synthesis section respectively.

It is preferable that between the synthesis gas section and the synthesis section there should be provided a once-through reactor for synthesis of the product, and a separation unit for the separation of a product-rich fraction to a line and a product-poor fraction to a line leading to the synthesis section.

Furthermore, it is preferable that the processing plant should also comprise a separate secondary synthesis gas line for producing a secondary synthesis gas, and a line for conveying the secondary synthesis gas as feed for the synthesis section.

BRIEF DESCRIPTION OF THE DRAWINGS

The invention will be described below with the aid of an example and the attached figures, wherein:

FIG. 1 is a schematic illustration of the structure of a traditional plant for the production of methanol from natural as.

DETAILED DESCRIPTION OF THE PREFERRED EMBODIMENTS

Figure 1:
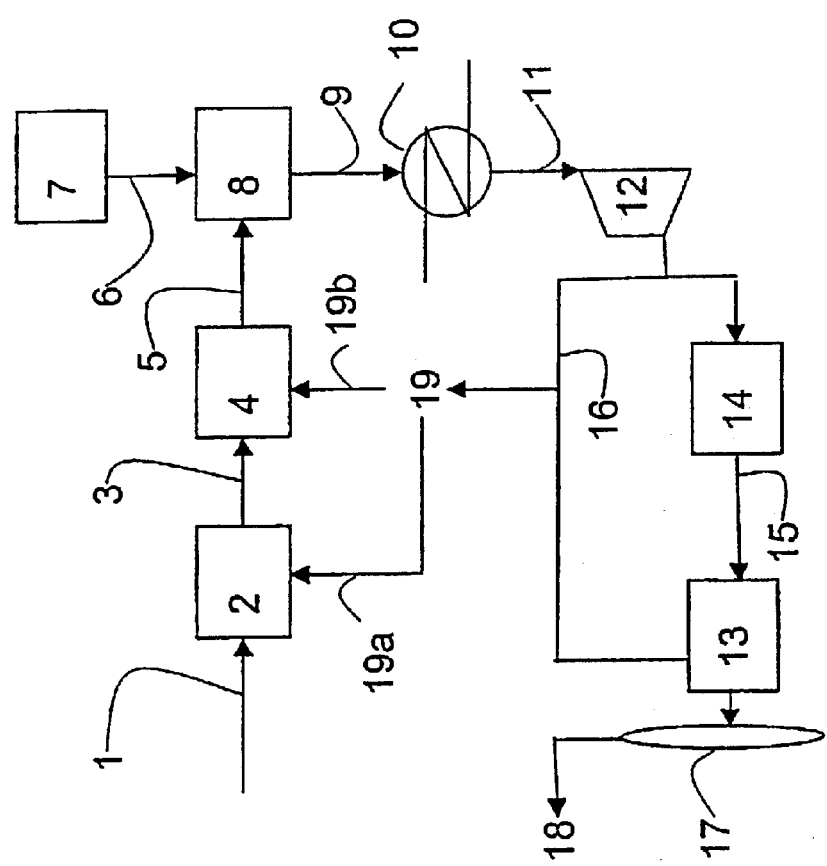

Today, the production of methanol is carried out essentially as shown in the schematic diagram in FIG. 1. The processing plant consists basically of three sections, a synthesis gas section 2, 4, 8) where production is normally based on natural gas (NG), a synthesis section 14 where the actual methanol synthesis takes place, and a distillation section 17 where the methanol produced is purified.

The methanol synthesis takes place by means of the two following reactions:

1) $CO+2H_2=CH_3OH$, or
2) $CO_2+3H_2=CH_3OH+H_2O$

The synthesis gases, which essentially comprise CO, $CO_2$ and $H_2$, in addition to water and non-reacted hydrocarbons, are prepared following one of three different concepts, namely:

a) conventional steam reforming,
b) conventional autothermal reforming with a catalyst (ATR) or without a catalyst (POX), or
c) a combination of a) and b).

Before the natural gas is sent in line 1 to the reformer for synthesis gas production, sulphur compounds are removed in a conventional manner, and steam is then saturated in and/or added directly to the gas. Saturation can also take place by using a so-called "saturator". Normally, the gas is also treated in a so-called pre-reformer 2 before it is sent into the reformer 4, 5, in order to convert all higher hydrocarbons.

The following chemical reactions take place during the production of synthesis gas.

3. $CH_3+H_2O=CO+3H_2$, steam reforming
4. $CH_4+1.5O_2=CO+2H_2O$, partial oxidation
5. $CO+H_2O=CO_2+H_2$, shift reaction Reactions 3 and 5 in the reforming reactor are highly endothermic and the heat that is necessary for the reaction can either be supplied by external firing, as in a steam reformer, or by means of a combination with partial oxidation, according to reaction 4, as in an autothermal reformer.

In a steam reformer (SR), natural gas (NG) (methane) is converted in a tubular reactor at a high temperature and a relatively low pressure. A traditional steam reformer consists of a large number of reactor tubes, usually 100 to 1000, having a tube length of 10–16 meters, where each tube has an internal diameter of about 10 cm and an external diameter of about 12 cm. This unit may have a length of as much as 50 meters, a width of more than 10 meters and a height of more than 20 meters, with the result that such a reactor will require a relatively large space.

Conventional steam reformers are operated in a pressure range of from about 15 to 40 bar. The outlet temperature from such a reformer may be as much as 950° C. The heat required to operate the reaction is supplied by means of external firing or heating and the reformer can be top, bottom or terrace-fired. The heat can also be transferred to the reaction by means of convective heat as in a heat exchange reactor. The ratio of steam to carbon is from 1.6 to 4 and the ratio of $H_2$ to CO in the product stream from the reformer is about 3. A typical synthesis gas from a conventional steam reformer contains about 3 volume % methane.

In an autothermal reformer (ATR), synthesis gas production is carried out mainly by means of reactions 3 and 4, so that the heat necessary for reaction 3 is generated internally by reaction 4. In an ATR, natural gas (methane) is brought together with oxygen-containing gas such as, for example, air, inside a combustion chamber. The temperature in the combustion chamber may rise to more than 2000° C. After the combustion, the reactions are brought into equilibrium by means of a catalyst before the gases exit the reformer at a temperature of about 1000° C. The size of an ATR may be a height of 10–20 meters and a diameter of about 4–7 meters.

An alternative autothermal reformer uses a concept called partial oxidation (POX). A reformer of this kind does not contain a catalyst to expedite the reactions and therefore as a rule will have larger dimensions than an ATR.

The reforming of natural gas can also be effected by combined reforming (CR), where the reformer section consists of an SR and an ATR. A combination of SR and ATR makes it possible to adjust the composition exiting the reformer section by controlling the admissions of the two reformers. In CR, SR is operated under milder conditions than in normal SR, i.e., at a slightly lower temperature. This results in a slightly higher methane content in the as released from the reformer. This methane content is converted in the subsequent ATR. The ratio of carbon to steam in a reformer of this kind is in the range of 1.2 to 2.4, with a ratio of hydrogen to CO in the product gas of well over 2. The optimal stoichiometric number $(SN=(H_2-CO_2)/(CO_2+CO))$ for methanol synthesis is about 2.05.

FIG. 1 shows a synthesis gas section of the CR type. However, ills not critical what type of synthesis gas section is included in the plant. A plant equipped with a synthesis gas section of the ATR type will not have SR 4, whereas a plant of the SR type will not have an ATR 8 and air separation unit 7 with accompanying line 6.—

After the synthesis gas section 2, 4, 9, the synthesis gas is conveyed in line 9 to a heat exchanger 10 where it is cooled. After the heat exchanger 10, the synthesis gas is conveyed in line 11 to a compressor 12 where it is compressed to the desired pressure in the methanol synthesis section, which is typically about 80 bar.

The methanol synthesis in the synthesis section takes place according to reaction equations 1 and 2 above, and is an exothermic process where conventionally several different types of reactors 14 are used, such as:

An isothermal tubular reactor with catalyst on the inside of vertical tubes and boiling water on the outside. The reaction heat will be removed by partial evaporation of the water.

Adiabatic fixed bed reactors with cooling between each step

A fluidised bed reactor

Adiabatic reactors with cooling by means of a supply of new feed at several levels downwards in the reactor (quench converter system).

After the reactor 14, the product is fed via a line 15 to a crude methanol separator 13 that separates the product stream into a methanol-rich stream 34 and a methanol-poor stream 16. The methanol-rich stream in line 34 is fed to a conventional methanol purification unit 17 that sends methanol out in line 18.

The methanol-poor product is usually led via a recycle line 16 back to the reactor 14. Alternatively, the reactor is a once-through reactor without recirculation that can be followed by one or more similar reactors placed in series.

A synthesis loop 13, 14, 15 and 16 is shown in FIG. 1. The actual recycle loop consists of a heat exchanger ("inter exchanger") (not shown) that preheats the feed to the synthesis reactor and cools the production gas, the synthesis reactor(s) 14, a crude methanol separator 13 and a system for recovering energy from the exothermic methanol synthesis reactions (not shown).

A so-called purge stream is taken out of this recycle loop via line 19 to prevent the accumulation of inert (non-reacting) gases in the recycle loop. The purge gas in line 19 is often split into a first stream 19a that is conveyed together with the feed gas in the gas supply 1 and a second stream 19b that is used as combustion gas for heat-consuming processes in the methanol synthesis, such as in the steam reformer 4, or in another process at the same plant, or is discharged.

One of the problems of the prior art is that inert gases, primarily nitrogen, in the recycled purge gas will react with other constituents of the synthesis gas and be converted to $NO_x$ and $NH_3$ at the high temperatures that prevail in the reforming plant. According to the present invention, this is avoided in that the portion of the purge gas that is rich in inert gas is used only as fuel for energy-consuming processes, such as the steam reformer 4.

Figure 2:
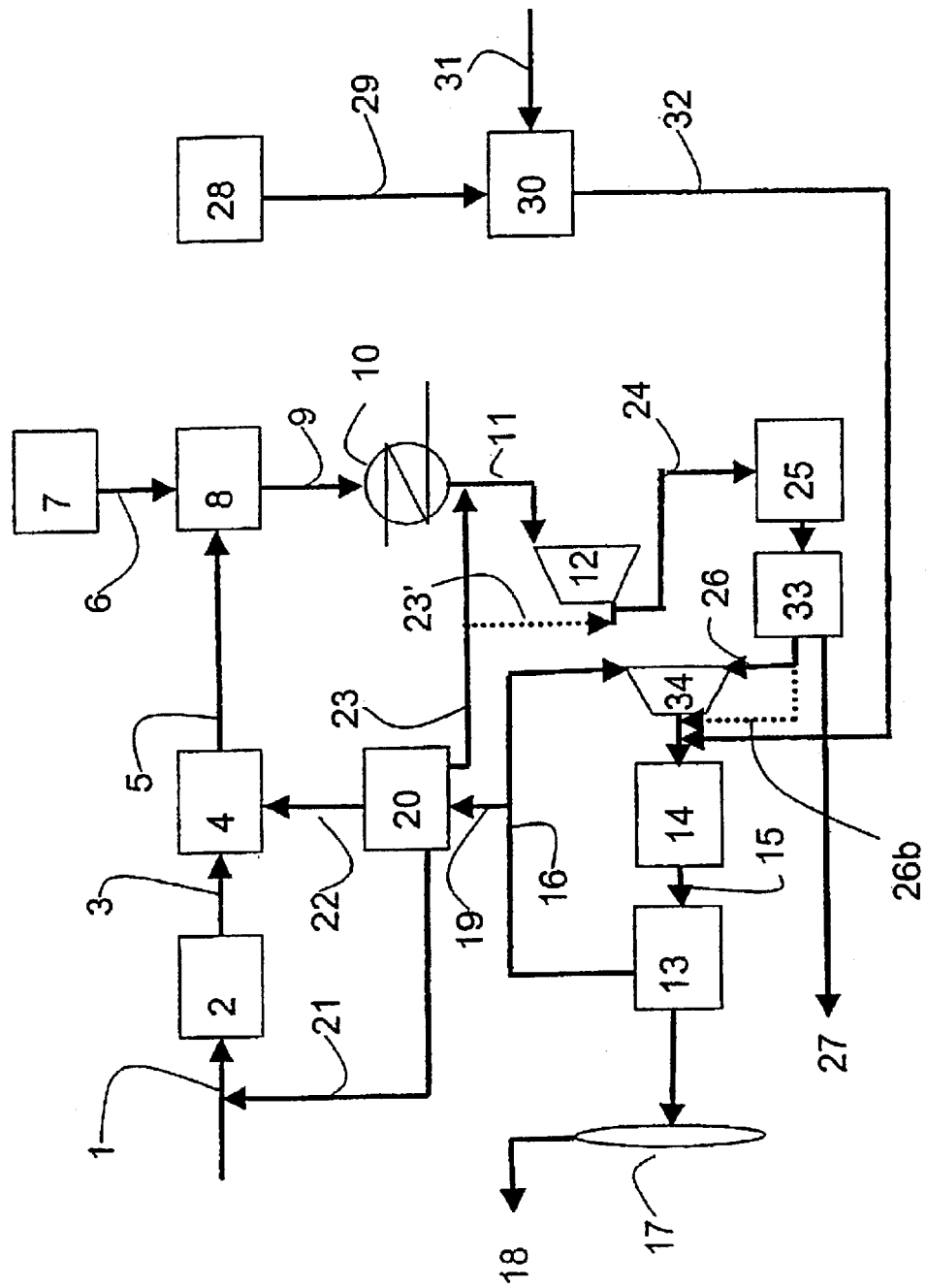
FIG. 2 is a schematic illustration of a plant according to the present invention.

FIG. 2 illustrates a preferred embodiment of the present invention which has been based upon a traditional existing methanol synthesis plant as described above. A plant having an existing reformer section based on CR has been taken as the basis.

In this embodiment, purge gas that is taken out of the recycle loop in line 19 is separated in a separation unit 20 into three streams, two hydrogen-rich gas-streams 21, 23 at different pressures, and a hydrogen-poor stream 22. The separation unit 20 is a conventional hydrogen recovery unit which either works according to the Pressure Swing Adsorption (PSA) principle, the membrane principle or is of a cryogenic type. The hydrogen-rich fractions preferably have a hydrogen content of 70 to 100%.

One of the hydrogen-rich streams 21 is fed into the gas supply 1 and is mixed with incoming natural gas. The other hydrogen-rich stream 23 is led into the synthesis gas stream in line 11. Alternatively, depending upon the relative pressures in the different parts, this hydrogen-rich stream 23 is led via line 23' into the synthesis gas stream after the compressor 12 inside a line 24. The hydrogen-poor stream 22 is sent to the burners in the steam reformer 4 as fuel.

Line 24 conveys the synthesis gas stream from the compressor 12 to an extra once-through reactor 25 for the production of methanol. This synthesis gas stream is enriched with hydrogen from line 23 or 23'. The reactor 25 will normally give a yield of about 30% methanol, that is to say that about 30–35% of the carbon entering the reactor is converted to methanol. The product stream from the reactor 25 is separated in a crude methanol separator 33 into a methanol-rich stream 27 and a stream 26 that consists primarily of non-reacted synthesis gas and inert gases from the methanol synthesis. Stream 26 is led into a recycle compressor 34 in the recycle loop 16 and is introduced into the existing reactor 14. Alternatively, if the pressure in line 26 is or is set sufficiently high, stream 26 can be fed as indicated at 26b past compressor 34 and directly to the recycle loop and reactor 14.

The stoichiometric number, SN, for the synthesis gas in line 9 will normally be about 2.06, whilst the SN in line 24 will normally be greater than 2.06 because of the supply of hydrogen-rich gas from line 23 or 23'. The methanol-poor stream 26 has a high hydrogen content in relation to other reactive gases, i.e . . . a high SN that normally will be greater than 2.10.

In order to reduce the SN of the gas from line 26, the recycle line 16 is also fed with a synthesis as having a lower SN produced in a separate secondary synthesis gas line 28, 29, 30, 31, 32. This secondary synthesis gas line comprises an ATR or POX reactor 30 which receives oxygen as almost pure $O_2$, oxygen-enriched air or air, via line 29 from the oxygen unit 28 and natural gas from line 31. This new synthesis gas is fed to the recycle line 16 through line 32. This secondary synthesis gas line could also include non-illustrated units such as a compressor and heat exchanger etc. The gas that is introduced into the reactor 30 is pretreated in the same way as the original synthesis gas line, 2, 4, 8. Surplus heat in the process can be used in the different separation steps: if desired, the natural gas feed to ATR or POX 30 can be heated by using an extra fire heater or heat exchanger using hot synthesis gas from ATR or POX 30.

A combination of preheating and steam reforming in a convective reformer before ATR or POX 30 is also conceivable.

Here, it is important that the new separate ATR or POX reactor 30, which produces a synthesis as having an SN of less than 2, has a capacity sufficient to allow the SN of the feed to the synthesis reactor 14 to be reduced to about 2.06 from an SN of more than 2.10 in the gas in line 26.

The once-through reactor 25 is usually a once-through reactor of the simplest possible type i.e., of the isothermal tubular reactor type as mentioned above with reference to reactor 14, and will on the outside of the tubes of the reactor produce more than enough steam at the right pressure to obtain a favourable steam to carbon ratio inside the reformer. Normally, 30 to 40% of the steam generated on the outside of the tubes in the reactor 25 for the cooling thereof will be used as feed for the new reformer 30 in order to obtain the desired steam/carbon ratio therein. The rest of the steam can be used in other steam and/or heat consuming processes, such as, for example, for purifying ! further processing of the methanol stream. Typically, the methanol-rich product stream contains about 15% water and some ethanol, and distillation is usually carried out in order to obtain pure methanol.

The conversion in the new reactor 25 will affect the conversion in the existing synthesis reactor 14 so that a reduced conversion in reactor 25 will lead to more unconverted synthesis gas being fed from reactor 25 to the synthesis reactor 14, with the result that there will be an increase in the methanol production in 14. The amount of the gas in the recycle line 16 that is taken out as purge gas through line 19 and the amount that is recycled in line 16 directly to the synthesis reactor 14 can be varied in order to optimise the system.

EXAMPLES

The table below shows simulation results for two examples, one for an existing methanol process according to the outline in FIG. 1, and one for a plant according to the present invention.

The basis for the simulation is natural as having a methane content of about 82% methane. The oxygen feed is varied so that the $CH_4$ slip is about 1.36%. The admissions in the existing reformer section are the same in both examples.

The new ATR operates at 35 bar and the steam to carbon ratio (S/C) to the pre-reformer in the new line II is 1.0. The once-through reactor 25 is positioned after the compressor 12 and has an outlet pressure of 80 bar.

| | | Example 1 Existing methanol process | Example 2 New concept for increased methanol production |
|---|---|---|---|
| Line I | | | |
| NG-rate to existing line | Normalised (%) | 100 | 100 |
| NG-fuel | % | 100 | 100 |
| Oxygen to secondary reformer 8 | % | 100 | 110 |
| S/C in feed to reformers 4, 8 | % | 1.8 | 1.8 |
| Temperature in primary reformer 4 | | | |
| Duty | % | 100 | 100 |
| Temperature in secondary reformer 8 | ° C. | 1000 | 1000 |

-continued

|  |  | Example 1 Existing methanol process | Example 2 New concept for increased methanol production |
|---|---|---|---|
| Line II |  |  |  |
| NG-rate to ATR line 31 | % in relation to existing plant |  | 26 |
| S/C feed to new pre-reformer |  |  | 1 |
| Oxygen to new ATR 30 | % in relation to existing plant |  | 40 |
| Inlet temperature in new ATR 30 | ° C. |  | 600 |
| Outlet temperature in new ATR 30 | ° C. |  | 1000 |
| Outlet pressure from new ATR 30 | bar |  | 35 |
| $CH_4$ slip from new ATR 30 | mol % |  | 1.4 |
| Stoichiometric number |  |  |  |
| SN 1. line I from pre-reactor |  |  | 2.13 |
| SN 2. line I, feed pre-reactor |  |  | 2.08 |
| SN 4. line II from new ATR 30 |  |  | 1.68 |
| SN from CR, line 9 |  |  | 2.02 |
| SN 3. line I + II, MUG to synthesis loop |  |  | 2.06 |
| Synthesis loop |  |  |  |
| Recycle ratio in synthesis loop |  | 4.2 | 4.2 |
| Total consumption and production |  |  |  |
| Total NG to main process | % | 100 |  |
| Total $O_2$-consumption | % | 100 |  |
| Total production of crude methanol, I + II (methanol content in the crude methanol) | % | 100 | 126 |

As can be seen from the table above, it is possible in the illustrated example to substantially increase the production of crude methanol in a process plant for methanol production, without subjecting the original plant to more stresses than during traditional operations. This is primarily of importance for extensions of existing plants where it is desirable to use the existing plant to the greatest extent possible, without having to redimension and rebuild large parts of the existing plant.

For the modified plant, it is possible to use surplus materials or unconverted amounts of a type of reactants in the process by supplying new amounts of other reactants and thus increase production, thereby rendering it less expensive.

It is important to note that the layout of the individual modules and constituents in the exemplified plants may differ from that which initially can be understood from the figures. Elements that the skilled person knows are included or can be included in such plants, such as heat exchangers, compressors, pressure-relief tanks etc., have to some extent been omitted as they are of no significance to the invention. Similarly, the assembly of some of the elements can differ. Thus, some of the elements that are drawn as one unit may consist of several similar or dissimilar elements connected in series and/or in parallel relation. For instance, the reactor 14 may comprise a plurality of parallel-connected and/or series-connected reactors.

The present method and process plant are also useful in connection with the extension of plants for the production of oxygenated hydrocarbons other than methanol, such as, for example, dimethyl ether. The construction and mode of operation of a plant for the production of dimethyl ether are quite similar to those of a plant for methanol production, and thus the problems are completely parallel. Although the invention has been described with reference to a plant for the production of methanol, it also comprises other plants as mentioned above.

What is claimed is:

1. A method for increasing production in an existing process plant for converting natural gas to a product, comprising:
    converting the natural gas into a synthesis gas in a synthesis gas section, the synthesis gas being reacted in a reactor for synthesis of the product;
    separating non-converted synthesis gas and product into a product-rich stream and a product poor stream;
    removing the product-rich stream from the process;
    recycling the product-poor stream as feed in a recycle loop to the reactor together with make-up synthesis gas;
    removing a portion of the recycle stream from the recycle loop as a purge gas;
    separating the purge gas into a hydrogen-rich stream and a hydrogen-poor stream, the hydrogen-rich stream being introduced into the process plant where it is desirable to have a supplement of hydrogen; and
    feeding the synthesis gas with the hydrogen-rich stream as a hydrogen-enriched synthesis gas from the separated purge gas, the hydrogen-enriched synthesis gas being passed through a once-through reactor for production of the product and through a unit in order to separate the product-rich stream and the product-poor stream.

2. The method accordingly to claim 1, wherein the residual thermal value in the hydrogen-poor stream is used for heating before it is discharged.

3. The method according to claim 1, wherein the product-poor stream is fed with additional synthesis gas which is produced in a separate secondary synthesis gas line.

4. The method according to claim 1, wherein the reactor is an existing reactor in the process plant and is operated virtually unchanged.

5. The method according to claim 2, wherein the reactor is an existing reactor in the process plant and is operated virtually unchanged.

6. The method according to claim 3, wherein the reactor is an existing reactor in the process plant and is operated virtually unchanged.

7. The method according to claim 1, wherein the converting of the synthesis gas is based on one of ATR and POX.

8. The method according to claim 2, wherein the converting of the synthesis gas is based on one of ATR and POX.

9. The method according to claim 3, wherein the converting of the synthesis gas is based on one of ATR and POX.

10. The method according to claim 1, wherein the product is one of methanol and dimethyl ether.

11. The method according to claim 2, wherein the product is one of methanol and dimethyl ether.

12. The method according to claim 3, wherein the product is one of methanol and dimethyl ether.

13. A processing plant for producing a product on the basis of natural gas, comprising:

a synthesis gas section;

a synthesis section in communication with the synthesis gas section that is arranged to form the product;

a purification section in communication with the synthesis section and arranged such that the product is separated from unconverted reactants and other substances and purified, and wherein unconverted reactants that are separated from the product are recycled to the synthesis section, and where at least a portion of the gas that is recycled is drawn off;

a separation unit arranged to separate the gas that is drawn off into hydrogen-rich and hydrogen-poor fractions;

the hydrogen-rich fractions leading into the natural gas feed and for recycling to the synthesis section; and a once-through reactor for synthesis of the product, wherein feeding the synthesis gas with the hydrogen-rich fraction as a hydrogen-enriched synthesis gas from the drawn off gas, the hydrogen-enriched synthesis gas is passed through the once-through reactor for production of the product and through a unit to separate a product-rich fraction and a product-poor fraction.

14. The processing plant of claim 13, further comprising a line for conveying hydrogen-poor fractions for combustion.

15. The processing plant according to claim 13 further comprising a separate secondary synthesis gas line for producing a secondary synthesis gas, and a line to lead the secondary synthesis gas as feed for the synthesis section.

* * * * *

UNITED STATES PATENT AND TRADEMARK OFFICE
CERTIFICATE OF CORRECTION

PATENT NO. : 6,794,418 B2  Page 1 of 1
APPLICATION NO. : 10/169420
DATED : September 21, 2004
INVENTOR(S) : Sogge et al.

It is certified that error appears in the above-identified patent and that said Letters Patent is hereby corrected as shown below:

COLUMN 2

Line 11, delete "existin" and substitute therefor --existing--.
Line 53, delete "as" and substitute therefor --gas--.

COLUMN 4

Line 8, delete "as" and substitute therefor --gas--.
Line 16, delete "ills" and substitute therefor --it is--.
Line 20, delete "6.-" and substitute therefor --6.--.
Lines 43, 44, delete "34", each occurrence.

COLUMN 5

Line 53, delete "as" and substitute therefor --gas--.

COLUMN 6

Line 5, delete "as" and substitute therefor --gas--.
Line 20, delete "purifying ! further" and substitute therefor --purifying further--.
Lines 30-34, beginning with --The amount-- this should begin a new paragraph.
Line 41, delete "as" and substitute therefor --gas--.

Signed and Sealed this

Twenty-third Day of September, 2008

JON W. DUDAS
*Director of the United States Patent and Trademark Office*